United States Patent [19]

Douwens et al.

[11] Patent Number: 4,829,997
[45] Date of Patent: May 16, 1989

[54] PORTABLE HEAT EXCHANGER FOR INHALATION REWARMING

[75] Inventors: Robert J. Douwens; John S. Hayward, both of Victoria, Canada

[73] Assignee: University of Victoria, Victoria, Canada

[21] Appl. No.: 161,444

[22] Filed: Feb. 18, 1988

[51] Int. Cl.$^4$ .................. A62B 7/00; A62B 7/10; A61M 16/00
[52] U.S. Cl. .................. 128/201.13; 128/204.17; 128/204.13; 128/203.26
[58] Field of Search ............... 128/202.13, 203.26, 128/204.17, 202.26, 203.17, 203.27, 204.13, 400, 202.12, 203.12, 203.16, 201.13; 55/DIG. 33; 422/49; 165/132

[56] References Cited

U.S. PATENT DOCUMENTS

| | | | |
|---|---|---|---|
| 2,610,038 | 9/1952 | Phillips | 128/201.13 |
| 3,326,214 | 6/1967 | McCoy | 128/201.13 |
| 3,747,598 | 7/1973 | Cowans | 128/201.13 |
| 4,319,566 | 3/1982 | Hayward et al. | 128/203.26 |
| 4,355,636 | 10/1982 | Oetjen et al. | 128/204.13 |
| 4,597,917 | 7/1986 | Lunsford | 128/204.17 |
| 4,652,408 | 3/1987 | Montgomery | 128/204.13 |

Primary Examiner—Edgar S. Burr
Assistant Examiner—Kimberly L. Asher
Attorney, Agent, or Firm—Louis Weinstein

[57] ABSTRACT

A heat exchanger, particularly useful as an inhalation rewarming apparatus for the treatment of hypothermia is provided herein. It includes an insulated container having one or more air inlets leading from lateral faces thereof to longitudinal inlet passages, then to transverse connecting passageways from the inlet passageways, and finally via a longitudinal hollow outlet conduit in the core thereof to an air outlet. A thermochemical heat source is disposed within the core of the container, such thermochemical heat source delineating two boundaries of the hollow outlet conduit and one boundary of each of the inlet passageways. A wrapping of a wettable, absorbent material encases the thermochemical heat source, such wrapping providing the actual above described boundaries. A loose filling or an air-permeable porous material having a large surface area and high heat capacity and high heat conductivity is disposed in the above-described passageways and outlet conduit. In this way, air passing from the air inlet follows along a path through the above-described passageways and outlet conduit in heat- and vapor-transfer contact with the loose filling and the wrapping, so that air emerging from the air outlet is both heated and humidified.

8 Claims, 1 Drawing Sheet

U.S. Patent
May 16, 1989
4,829,997
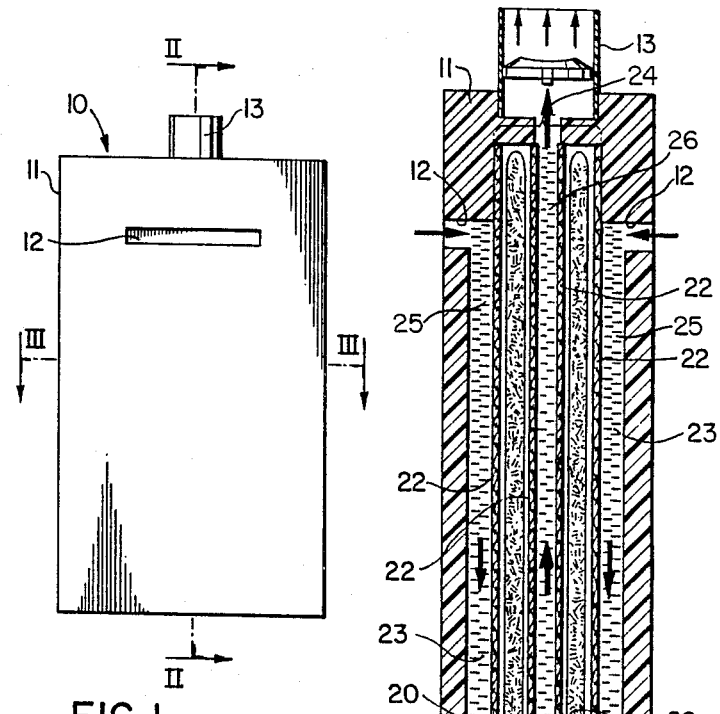
FIG. 1
FIG. 2
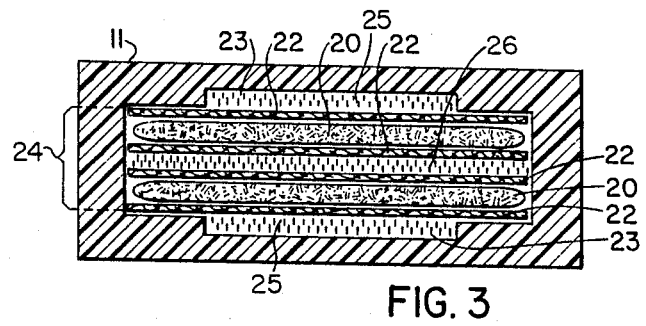
FIG. 3

PORTABLE HEAT EXCHANGER FOR INHALATION REWARMING

BACKGROUND OF THE INVENTION (i) Field of the Invention

This invention relates to a heat-exchanger in the form of a novel device for providing high efficiency of heat transfer from thermochemical heat sources to a flow of air, which device is especially useful for inhalation warming of hypothermia victims.

Hypothermia is one of the most frequently encountered and yet often overlooked aspects of emergency medicine. Hypothermia, like other medical conditions, is graduated by the degree of severity and the symptoms and urgency of treatment may differ radically at different levels. In mild hypothermia above 35° C. (95° F.), the accepted treatment is passive rewarming by natural or endogenous heat generation, which is simple, requires no equipment (other than a warm environment and/or blanket), and has no inherent morbidity. Moderate hypothermia occurs in the range of 32° to 35° C. (89.6° to 95° F.) and may produce loss of motor control, slurred speech and amnesia; marked hypothermia occurs at body core temperatures from 28° to 32° C. (82.4° to 89.6° F.) and is indicated by muscle rigidity, peripheral cyanosis and shock; and severe hypothermia occurs at temperatures from 25° to 28° C. (77° to 82.4° F.) at which the victim may have lost deep tendon reflexes and ventricular fibrillation and may appear dead with no palpable pulse or audible heartbeat. Body temperatures below 25° C. (77° F.) cause cardio-pulmonary arrest and death. These forms of hypothermia clearly present life-threatening medical problems complicating the treatment of the victim.

It is becoming established that the safest and most efficient technique for treating the severely hypothermic victim is by active core rewarming, i.e. the delivery of heat primarily to the body core or central circulation system (and also avoiding simultaneous rapid rewarming of the skin and extremities). Only inhalation rewarming is a suitable technique for use by paramedics and other trained emergency rescue personnel at a rescue site or during transport to hospital or clinical facilities.

Warm, moist air is also very useful for relieving laryngectomy and tracheotomy patients, and to relieve asthmatic bronchial spasms.

In the normal breathing process, inhaled air becomes warmed and humidifies as it passes through the nasal, tracheal and bronchial passages. This basic body function protects the delicate membranes in the lungs, but may not be sufficiently effective in heavy or rapid breathing of very cold dry air. During exhalation, some heat and moisture is returned to the walls of the breathing passages, but most of the heat energy and moisture is lost in the exhaled gases.

At rest and at a comfortable room temperature, the energy loss is of the order of 1 Kcal per hour, and is easily compensated by normal body functions. However, at low temperatures and high altitudes, the energy loss could be 230 Kcal and 250 grams of water per hour. This is a significant portion of the energy output of the body and contributes to the harmful effects caused by the inhalation of extremely cold air. In the absence of the ingestion of food, the mere use of warm clothing may not be sufficient to retain a desirable amount of the energy. Also, since thirst response is suppressed by extreme cold, desiccation could become a problem.

There is thus a widespread need for apparatus capable of producing heated and moist air, and in most cases such need is for air heating apparatus which is self-contained and not requiring mass electric power, compact, safe and not needing a flame to heat the air, and lightweight so as to be conveniently portable. As discussed above, one important current need for such air heating apparatus is to produce heated air to be inspired by persons through a suitable device into the lungs, which is an efficient means for warming persons suffering from body core heat loss that may have reached the stage of hypothermia. Such inspiration of heated air directly into the lungs is the most effective and safe way to warm a person and to bring hospital-type treatment to the rescue situation.

(ii) Description of the Prior Art

A number of devices have been developed in the prior art for the purpose of reducing the harmful or dangerous effects caused by the inhalation of extremely cold air. Such patented devices and techniques for heating and humidifying breathing gases have been devised for many purposes. In the field of conditioning inhalent gases and vapors, for use in underwater environments, U.S. Pat. No. 3,107,669 patented Oct. 22, 1963 by G. E. Gross may be mentioned. In that patent, the portable underwater breathing apparatus included an air inlet valve and a tubular extension adjacent the air inlet valve, with an air-treating, electric heating element sealingly disposed in that tubular extension.

U.S. Pat. No. 3,898,978 patented Aug. 12, 1975 by D. L. Marcus provided a self-contained, portable breathing gas heating system to be used by a diver for prolonged submersion in a cold environment. That device included a Vortex tube used for supplementary heating of the compressed breathing gas, a heat exchanger in an insulated container, a preheated fluid through which the breathing gas circulates in tubes, and exterior tubes for heat exchange of the gas with the environment.

U.S. Pat. No. 4,014,384 patented Mar. 29, 1977 by D. L. Marcus provided a self-contained, portable breathing gas heating system to be used by a diver for submersion in a cold environment. That device included a heat exchanger in an insulated container. The heat exchanger was in contact with preheated liquid through which the breathing gas circulated in tubing connecting the breathing gas source (tank) to the breathing outlet, which was secured in the mouth of the diver.

In the field of conditioning inhalent gases in a hospital environment, mention can be made of U.S. Pat. No. 3,902,486 patented Sept. 2, 1975 by P. Guichard. That patent provided a portble nasal diffuser comprising a respiratory assembly having a nasal mask to be worn over the nose, the assembly being provided with an air inlet and an outlet. Air was carried to pass through a filter material to the respiratory assembly and to the user. The filter could be heated by a suitable energy source or by the body of the user.

U.S. Pat. No. 4,016,878 patented Apr. 12, 1977 by D. Castel, which provided a heater and humidifier for use with a breathing mask or other breathing apparatus, to avoid unpleasant and injurious effects of prolonged breathing of cold dry air, or other breathing gas mixture. The patented device required injection and combustion of hydrogen directly in the breathing gas. In addition to the heating effect, the hydrogen combined with oxygen in the breathing gas to produce moisture.

U.S. Pat. No. 4,355,636 patented Oct. 26, 1982 by Oetjen et al provided a humidifier and heater for air to be inhaled for connection to an inhalation conduit of a respirator. That respirator included a housing having a bundle of vapor-permeable fiber tubes which had evaporation fiber wall surfaces exending therethrough. A packing was arranged adjacent each end of the housing in the tubes and sealed the space in the housing around the tubes between the packing. The tubes in the interior of the housing in the space had an exterior coating of either copper or silver. Warm water was circulated into the housing in the space around the tubes and the inhalation air was directed through the tubes, or vice versa.

U.S. Pat. No. 4,635,630 patented Jan. 13, 1987 by Noir et al provided an apparatus for heat therapy by inhalation which incorporated an enclosure designed to contain water in which two electrodes were immersed, and which were connected to an alternating current source. A tube terminating in a nozzle connected the top of this enclosure to a venturi which was connected upstream to the atmosphere and downstream to an inhalation mask, so as to form an air/water vapor mixture at a controlled temperature.

U.S. Pat. No. 4,652,408 patented Mar. 24, 1987 by Montgomery provided an inhalation apparatus which included a humidifier including a chamber having an inlet and an outlet. The chamber was releasably attached to a heater unit including a heater and a heat sensor. When the chamber and the heater unit were assembled together, the heater was in thermal contact with a heat transfer surface of the chamber at or adjacent the inlet port, while the temperature sensor was in thermal contact with the heat transfer surface at or adjacent the outlet port.

In the field of inhalation rewarming, mention may be made of U.S. Pat. No. 4,019,511 patented Apr. 26, 1977 by P. N. Choporis et al which provided a portable conditioned heated air breathing device for personal breathing for persons having respiratory problems. That device included a compartmented canister with a collapsible hose storage compartment, an air conditioning compartment and a heating compartment. It also contained an ejector for ejecting an additive into the conditioned air, as well as a structural arrangement for mixing fresh air with heated air. A filter was provided for filtering the air, and a device was provided for igniting a burner from the outside of the canister. A manually-controllable valve was provided for controlling the flow of fuel to the burner.

U.S. Pat. No. 4,245,631 patented Jan. 20, 1981 by R. A. Wilkinson et al provided a frigid air respirator to enable persons with physiological deficiencies such as cardiac or respiratory ailments to be active in frigid environments without subjecting their respiratory systems to the stress created by inhaling cold ambient air. The respirator comprising a cylindrical housing affixed to a face mask, constructed so as to permit the passage of air upon inhalation by the user into the chamber formed by the housing. A heating means was situated within the housing to increase the temperature of incoming air by radiation and a transversely positioned intake valve governed the admission of air into the respiratory tract of the user and divided the chamber formed by the housing into an internal chamber, which was contiguous with the mask cavity, and into a receiving chamber, wherein a supply of previously heated air was stored prior to inhalation. An exhaust valve was encompassed into the device to allow the expulsion of air from the internal chamber and mask cavity.

U.S. Pat. No. 4,319,566 patented Mar. 16, 1982 by Hayward et al provided an apparatus which delivered warm, water-saturated air or oxygen directly to the head, neck and thoracic core as the strategic body area to minimize "afterdrop" and gradual rewarming of core temperature without stimulating return of peripheral blood with high acidity and potassium concentration. The patented apparatus included a steam heat generating apparatus.

U.S. Pat. No. 4,430,994 patented Feb. 14, 1985 by B. E. Clawson, provided a respiratory gas heating and humidifying apparatus which made use of a humidifying element. Water was made to flow, as a film, over a heat transfer element. The respiratory gas was flowed over the water film and became more humid as it proceeded. As humidity increased during the course of flow, increased temperature was required to accomplish further humidification and so the gas temperature was increased as the humidity was increased.

U.S. Pat. No. 4,491,130 patented Jan. 1, 1985 by Dragerwerk Ag provided an emergency respirator for rapid use by a person. The emergency respirator included a container having a cartridge for material which acts to bind carbon dioxide and to liberate oxygen to gases which pass therethrough. A breathing connection was connected to one end of the container which terminated at its outer end in a mouthpiece and which defined a breathing passage interconnected into the cartridge. A jacket defined a heat storage connection to the opposite end of the container which was openable to the atmosphere. Expiration gases passed through the cartridge and were heated by the binding of the carbon dioxide. This heat was stored in the heat storage. Inspiration gases were then directed through the heat storage where they were heated before passing through the cartridge to liberate oxygen so that the incoming inspiration gases were enriched with oxygen and were heated before they were delivered to the person.

U.S. Pat. No. 4,597,917 patented July 1, 1986 by K. S. Lansford provided a highly portable means for warming and humidifying therapeutic gas to be administered to a patient. The apparatus included means for passing the therapeutic gas through an area heated by a chemical reaction which requires no outside energy source. The heated area may have included water, resulting in both heating and humidifying of the therapeutic gas. The chemical heating means involved mixing two or more chemicals to produce an exothermic reaction.

U.S. Pat. No. 4,601,287 patented July 22, 1986 by G. H. Royce Jr. provided a heated survival face mask fabricated from an air-impervious material, having a single forward protrusion forming a pivoted ambient air intake and exhaust orifice, which contained a heating element to elevate the temperature of the incoming ambient air, and which was designed to direct all of the exhausted air over the heating element, thereby to increase its efficiency.

U.S. Pat. No. 4,621,633 patented Nov. 11, 1986 by D. D. Bowles et al provided a heated oxygen system for emergency core rewarming in treating victims of severe hypothermia that includes a dry oxygen source, a separate heater compartment having an inlet connected to receive oxygen from the source, first heater means for heating the oxygen in the heater compartment, a resuscitator hose and mask connected to the outlet of the heater compartment, and second heater means for maintaining a predetermined temperature of the heated oxygen delivered to the resuscitator mask. A portable equipment case was provided for housing the oxygen system including the power source and heater controls therefor and other emergency airway equipment and supplies.

U.S. Pat. No. 4,662,352 patented May 5, 1987 by E. R. Aviles provided a catalytic heater for heating air, that contains a small percentage of hydrogen. A preheat catalytic chamber was provided within a primary catalytic chamber, and the air/hydrogen mixture was first flowed through the preheat chamber and then through the primary chamber, so that the gas was first catalytically preheated as it passed through the preheat chamber and was further heated with increased thermodynamic efficiency because of the preheating as it passed through the primary chamber. The preheat chamber was provided within massive heat sink means, preferably of brass, which obtained additional heat from the primary catalytic chamber so as to cause the preheat catalytic activity to be even further effective for overall increased thermodynamic efficiency of the system. The heat sink characteristic stabilized the output temperature of the heated gas against fluctuations.

Canadian Pat. No. 1,054,480, patented May 15, 1979 by Dragerwerke, Ag provided a filter respirator for self-protection against carbon monoxide and which had a catalyst portion which operated at high temperatures and a mouthpiece casing portion which was openable to cool respirated air by the evaporation of the saliva of the user. The respirator had a casing with an air inlet and an internal passage filled with a catalyst material and a mouthpiece casing connected to the catalyst casing with a passage for a flow of air from the catalyst casing through the mouthpiece casing. The mouthpiece portion casing contained an internal heat exchanger chamber filled with a plastic material of low thermal conductivity in the form of fibres, chips, screens, granules, balls or tubes, through which the exhaled air was passed so that the saliva adhered to the material. The subsequent inhaled air was cooled by the evaporation of the saliva. An exhalation valve was connected to the passage downstream of the passage with respect to exhalation gas flow.

Accordingly, as noted above, various techniques have been developed for heating and humidifying breathing gas, but these techniques and devices were usually complex and heavy. Thermal heaters required power sources, and were not particularly efficient in their use of energy. In a dry atmospheric environment, a humidifier must also contain stored water in some form and was thus usually heavy and bulky. For convenience and reliability such apparatus should be simple, compact and require a minimum of storable, energy-producing medium and water.

Despite the many attempts as described above that have been made in the past to provide devices and appliances for heating air for personal breathing, and for inhalation rewarming, there is still a definite need for an improved portable, conditioned-air, breathing device containing a heating unit which will condition the air and which can be utilized over a long period of time.

Thus of the patents referred to above, U.S. Pat. No. 3,107,669 required a electric heater element sealed therein. U.S. Pat. Nos. 3,898,978 and 4,014,384 required a hot water heat exchanger to heat the air, with no provision for humidifying the air. U.S. Pat. No. 3,902,486 required special means to heat a filter through which the gas passed. U.S. Pat. No. 4,355,636 required a hot water heat exchanger to heat the air. U.S. Pat. No. 4,652,408 required both an electric heater and a heat sensor.

While the system of the Castel U.S. Pat. No. 4,016,878 did indeed heat the breathing air, it was much too slow in building up sufficient heat to reach a target temperature, and large temperature fluctuations occurred between inspiration and expiration. U.S. Pat. No. 4,019,511 of Choporis used a flame as the heat source and, for humidification, required manual injection of water by the user. U.S. Pat. No. 4,245,631 required flow-control valves. U.S. Pat. No. 4,430,994 requires a compressed source of breathing gas and also required electric power for heating. The portable inhalation gas heating apparatus of the Hayward et al U.S. Pat. No. 4,319,506 required an external gas source or electric power to warm the inhalation gases. U.S. Pat. No. 4,491,130 used a porous material for heat conservation but did not teach humidification of the inhalate. U.S. Pat. No. 4,597,917 required a compressed gas source for the inhalate, didn't use a porous heat exchange material, and for humidification had the disadvantage of requiring the heating of a relatively large amount of water. U.S. Pat. No. 4,601,287 required the use of a special heating element. U.S. Pat. No. 4,621,633 required the use of a separate heater compartment. U.S. Pat. No. 4,662,352 required the use of a preheat catalytic chamber as well as a heat-sink primary catalytic chamber.

Canadian Pat. No. 1,054,480 used a porous heat exchange material for cooling purposes.

SUMMARY OF THE INVENTION

(i) Aims of the Invention

One object of the present invention then is to provide a device for the inhalation rewarming of hypothermic victims while avoiding further initial cooling of the body core.

Another object of the present invention is to provide such a device which is highly portable and which would be lightweight and cheap to construct.

Yet another object of this invention is to provide such device which includes good insulation against heat loss to the environment.

Still another object of this invention is to provide such device in which a porous material is used to facilitate transfer of heat from a chemical reaction to the inhalate.

Still another object of this invention is to provide such device which is designed to provide an inhalate of the desired therapeutic temperature (about 40° C.–45° C.) over a long duration automatically, that is, without a need for thermal control means.

(ii) Statement of Invention

By this invention, a heat exchanger is provided for use as an inhalation rewarming apparatus comprising: an insulated container having air inlet means leading from lateral faces thereof to longitudinal inlet passages, to a transverse connecting passageway and then via a longitudinal hollow outlet conduit in the core thereof to an air outlet means; a thermochemical heat source disposed within the core of the container, the thermochemical heat source delineating two boundaries of the hollow outlet conduit, and one boundary of each of the inlet passageways; a wrapping of a wettable, absorbent material encasing the thermochemical heat source, the wrapping providing the actual said two boundaries of the hollow outlet conduit and the one boundary of each of the inlet passageways; and a loose filling of a porous, air-permeable material of a large surface area and having both high heat capacity and high heat conductivity disposed in the inlet passageways, in the transverse connecting passageway, and in the hollow outlet conduit; whereby, air passing from the air inlet follows along a path through the inlet passageways, through the transverse connecting passageway and through the hollow outlet conduit in heat-transfer and vapour-transfer contact with the loose filling and with the wrapping, whereby air emerging from the air outlet means is both heated and humidified.

In a preferred embodiment an inhalation rewarming apparatus is provided comprising a) a rectangular parallelepiped, synthetic plastic insulated container, having air inlet means leading transversely from lateral faces thereof, and longitudinally downwardly within inlet passageways, then transversely through a transverse connecting passageway across the bottom, and longitudinally upwardly through a hollow outlet conduit in the core thereof and thence to an air outlet means; a pair of spaced-apart heat packs providing a thermochemical heat source disposed within the core of the container, the heat packs delineating two boundaries of the hollow outlet conduit, and one boundary of each of the inlet passageways; a wrapping of a wettable, absorbent fabric material encasing the thermochemical heat source, the wrapping providing the actual two boundaries of the hollow outlet conduit and the one boundary of each of the inlet passageways; and a loose filling of air-permeable matted strands of copper or brass disposed in the inlet passageways, in the connecting passageway and in the hollow outlet conduit; whereby, air passing from the air inlet to the air outlet follows along a long path through the inlet passageways, through the connecting passageway and through the outlet conduit in heat-transfer and vapour-transfer contact with the loose filling and with the wrapping, whereby air emerging from the air outlet means is both heated and humidified.

(iii) Other Features of the Invention

Preferably, the thermochemical heat source comprises two spaced-apart, thermochemical heat packs.

The wettable, wrapping may be a woven or non-woven fabric. The large surface area, high heat capacity and high heat conductivity material usually comprises porous, matted strands of metal, e.g. copper or brass.

The outlet means preferably comprises a mouthpiece fitted with a one-way valve.

Preferably, the heat source, wrapping and casing are nestled within a rectangular parallelepiped container of insulative material, e.g. of a synthetic plastic material, i.e. Styrofoam.

BRIEF DESCRIPTION OF THE DRAWINGS

In the accompanying drawings,

FIG. 1 is a top plan view of one embodiment of the inhalation rewarming apparatus of this invention;

FIG. 2 is a longitudinal section along the line II—II of FIG. 1; and

FIG. 3 is a cross-section along the line III—III of FIG. 1.

DESCRIPTION OF PREFERRED EMBODIMENT

(i) Description of FIG. 1

As seen in FIG. 1, the inhalation rewarming apparatus 10 is in the form of a rectangular parallelepiped container 11 formed, e.g. of foamed plastic insulatable material, provided with two air inlet slots 12 in the parallel top and bottom faces (only the slot 12 in the top face being shown) and an outlet, preferably valved, mouthpiece 13, centrally disposed and connected to the inner core of the container 11.

(ii) Description of FIGS. 2 and 3

The heart of the inventive inhalation rewarming apparatus is a thermochemical heat source, shown more fully in FIGS. 2 and 3 as two spaced-apart, generally-rectangular thermochemical heat packs 20 disposed about the core 24. These thermochemical heat packs are well known in the art, and two examples of suitable such thermochemical heat packs are described in Canadian Pat. Nos. 1,010,331 and 1,124,140. Any commercially-available thermochemical heat pack may be used. The advantages of the use of these thermochemical heat packs will be described later.

Surrounding the heat packs 20 is a wrapping of a wettable, absorbent material, e.g. woven or non-woven naturally-occurring material or synthetic fabric. The purpose of such fabric is to maximize heat transfer and to provide water for the humidification of the air which passes out of the inhalation device 10. As well, wrapping 22 provides a boundary for inlet passageways 25 and for hollow outlet conduit 26, i.e. to provide a sinusoidal passageway 25/26.

Disposed within the passageways 25 and the hollow outlet conduit 26 are outer loose fillings 23 of an air-permeable material having a large surface area, having high heat capacity, and high heat conductivity, e.g. matted metal strands, such as copper or brass. This material rapidly and efficiently transfers heat to the air which passes through the inhalation rewarming device. The downward air flow in inlet passageways is combined in transverse connecting passageway 27 at baffle 21 at the bottom of the device 10 and flows up through hollow outlet conduit 26 which is in the core 24 of the device 10.

Operation of Preferred Embodiment

Thus, this preferred embodiment of the device utilizes two re-usable thermochemical heat-packs as the heat source and uses a meshwork of copper strands as the porous air-permeable material. The two packs provide sufficient heat when activated for approximately 30 min. of airway warming at a temperature of approximately 45° C.

The thermochemical heat packs are wrapped with a means for highly-efficient heat transfer from the heat packs to the air. Such means is the porous, air-permeable material having the large surface area, and both high heat capacity and high heat conductivity. In its preferred embodiment, the copper strands provide the large surface area for rapidly and efficiently transferring heat to the air passing through the channels.

The heat source, which is in close contact with the porous metallic material having the high heat capacity and the high heat conductivity, is also surrounded by, and is in close contact with, the water-saturated fabric. The use of a water-saturated fabric maximizes heat transfer to the porous material, as well as providing the water for humidification of the inhaled air.

Inhaled, ambient air is channeled (with low resistance to flow) through this porous material during the inspiratory phase of normal breathing, and is delivered to the respiratory tract via a mouthpiece or a breathing mask. The inhaled air is humidified and warmed to approximately 45° C. as a result of its passage through the heat exchanger. The exchanger is surrounded by heat insulative material e.g. a foamed plastic material to minimize heat loss to the environment.

Extended operation of this device is accomplishyed by simple replacement of heat packs. Re-wetting means (not shown) are also preferably provided for replacement of water evaporated from the fabric material which acts as the water reservoir and as the thermal-coupling system (for heat conduction) between the heatpacks and the copper strands which are in the air channels. This system also causes water to evaporate into the warmed air, which greatly increases its heat content. When inhaled, this warm, humidified air donates its heat (from the air itself and from condensation of water) to the respiratory tract and thence to the heart and other critical tissues.

No known device uses readily-available heat-packs as a source of heat for inhalation warming of hypothermia victims. These heat packs have a maximum temperature that is in a safe treatment range and thereby obviates the need for an automatic, high-temperature control device, or regulation by an attendant. This is particularly important for the transport phase of rescue operations, during which close monitoring of temperature can be impossible due to difficult transport conditions and/or shortage of manpower.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

What we claim is:

1. A heat exchanger for use as an inhalation rewarming apparatus comprising:
   (a) an insulated container having air inlet means leading from lateral faces thereof to longitudinal inlet passages, to a transverse connecting passageway and then via a longitudinal hollow outlet conduit in the core thereof to an air outlet means;
   (b) a thermochemical heat source disposed within the core of said container, said thermochemical heat source delineating two boundaries of said hollow outlet conduit, and one boundary of each of said inlet passageways;
   (c) a wrapping of a wettable, absorbent material encasing said thermochemical heat source, said wrapping providing the actual said two boundaries of said hollow outlet conduit and said one boundary of each of said inlet passageways; and a loose filling of a porous, air-permeable material of a large surface area and having both high heat capacity and high heat conductivity disposed in said inlet passageways, in said transverse connecting passageway, and in said hollow outlet conduit;

whereby, air passing from said air inlet follows along a path through said inlet passageways, through said transverse connecting passageway and through said hollow outlet conduit in heat-transfer and vapour-transfer contact with said loose filling and with said wrapping, whereby air emerging from said air outlet means is both heated and humidified.

2. The heat exchanger apparatus of claim 1 wherein said thermochemical heat source comprises two spaced-apart thermochemical heat packs.

3. The inhalation rewarming apparatus of claim 1 wherein said wettable, absorbent wrapping is a woven or non-woven fabric.

4. The heat exchanger apparatus of claim 1 wherein said large surface area, high heat capacity and high heat conductivity porous, air-permeable material comprises matted strands of metal.

5. The heat exchanger apparatus of claim 4 wherein said metal is copper or brass.

6. The heat exchanger apparatus of claim 1 wherein said outlet means comprises a mouthpiece fitted with a one-way valve.

7. The heat exchanger apparatus of claim 1 wherein said heat source, wrapping and casing are nestled within a rectangular parallelepiped, synthetic plastic, insulative container.

8. An inhalation rewarming apparatus comprising
   (a) a rectangular parallelepiped, synthetic plastic, insulated container having air inlet means leading transversely from lateral faces thereof, and longitudinally downwardly within inlet passageways, then transversely through a transverse connecting passageway across the bottom, and longitudinally upwardly through a hollow outlet conduit in the core thereof and thence to an air outlet means;
   (b) a pair of spaced-apart heat packs providing a thermochemical heat source disposed within the core of said container, said heat packs delineating two boundaries of said hollow outlet conduit, and one boundary of each of said inlet passageways;
   (c) a wrapping of a wettable, absorbent fabric material encasing said thermochemical heat source, said wrapping providing the actual said two boundaries of said hollow outlet conduit and said one boundary of each of said inlet passageways; and
   (d) a loose filling of air-permeable matted strands of copper or brass disposed in said inlet passageways, in said connecting passageway and in said hollow outlet conduit;

whereby, air passing from said air inlet to said air outlet follows along a long path through said inlet passageways, through said connecting passageway and through said outlet conduit in heat-transfer and vapour-transfer contact with said loose filling and with said wrapping, whereby air emerging from said air outlet means is both heated and humidified.

* * * * *

UNITED STATES PATENT AND TRADEMARK OFFICE
CERTIFICATE OF CORRECTION

PATENT NO. : 4,829,997

DATED : May 16, 1989

INVENTOR(S) : Robert J. Douwens and John S. Hayward

It is certified that error appears in the above-identified patent and that said Letters Patent is hereby corrected as shown below:

At Column 8, line 42, after "passageways" insert --25--

At Column 9, line 12, change "accomplishyed" to --accomplished--

Signed and Sealed this

Twenty-ninth Day of January, 1991

Attest:

HARRY F. MANBECK, JR.

Attesting Officer

Commissioner of Patents and Trademarks